US012702809B2

(12) United States Patent
Sharma et al.

(10) Patent No.: US 12,702,809 B2
(45) Date of Patent: Aug. 11, 2026

(54) TUOHY VALVE TIGHTENING PORT FOR PERCUTANEOUS CIRCULATORY SUPPORT DEVICE REPOSITIONING AND AXIAL LOCKING

(71) Applicants: Boston Scientific Medical Device Limited, Galway (IE); Boston Scientific Scimed Inc., Maple Grove, MN (US)

(72) Inventors: Neeraj Kumar Sharma, New Delhi (IN); Sumit Agrawal, Haryana (IN); Rupesh Kumar Pahwa, Gurugram (IN); Qian Liu, Plymouth, MN (US)

(73) Assignees: Boston Scientific Medical Device Limited, Galway (IE); Boston Scientific Scimed, Inc., Maple Grove, MN (US)

( * ) Notice: Subject to any disclaimer, the term of this patent is extended or adjusted under 35 U.S.C. 154(b) by 440 days.

(21) Appl. No.: 18/116,619

(22) Filed: Mar. 2, 2023

(65) Prior Publication Data

US 2023/0277833 A1 Sep. 7, 2023

Related U.S. Application Data

(60) Provisional application No. 63/316,239, filed on Mar. 3, 2022.

(51) Int. Cl.
*A61M 39/06* (2006.01)
*A61M 60/13* (2021.01)
(Continued)

(52) U.S. Cl.
CPC ........ *A61M 39/06* (2013.01); *A61M 39/0613* (2013.01); *A61M 60/13* (2021.01);
(Continued)

(58) Field of Classification Search
CPC .. A61M 39/06; A61M 39/0613; A61M 60/13; A61M 60/865; A61M 2039/0258;
(Continued)

(56) References Cited

U.S. PATENT DOCUMENTS 4,886,507 A 12/1989 Patton et al.
5,059,186 A 10/1991 Yamamoto et al.
(Continued)

FOREIGN PATENT DOCUMENTS

EP 3866876 B1 11/2022
JP H1085341 A 4/1998
(Continued)

OTHER PUBLICATIONS

International Search Report and Written Opinion for International Application No. PCT/US2023/014358, dated May 31, 2023. (18 pages).

*Primary Examiner* — Pamela M. Bays
(74) *Attorney, Agent, or Firm* — Seager, Tufte & Wickhem LLP

(57) ABSTRACT

A tightening port for use with a hub of an introducer sheath includes a cartridge for reversible engagement with a proximal end of the hub, the cartridge having a proximal end and a distal end and a lumen extending therebetween, a seal positioned within the lumen of the cartridge, a lock nut having an inner portion positioned within the lumen of the cartridge and an outer portion configured for engagement with the proximal end of the cartridge, such that the inner portion of the lock nut is configured to push the seal to reduce a size of an opening of the seal.

14 Claims, 8 Drawing Sheets

(51) Int. Cl.
*A61M 60/865* (2021.01)
*A61M 39/02* (2006.01)

(52) U.S. Cl.
CPC ... *A61M 60/865* (2021.01); *A61M 2039/0258* (2013.01); *A61M 2039/027* (2013.01); *A61M 2039/0273* (2013.01); *A61M 2039/062* (2013.01)

(58) Field of Classification Search
CPC .... A61M 2039/027; A61M 2039/0273; A61M 2039/062
See application file for complete search history.

(56) References Cited

U.S. PATENT DOCUMENTS

| | | | |
|---|---|---|---|
| 5,254,097 | A | 10/1993 | Schock et al. |
| 5,295,969 | A | 3/1994 | Fischell et al. |
| 5,324,271 | A | 6/1994 | Abiuso et al. |
| 5,935,112 | A | 8/1999 | Stevens et al. |
| 6,692,462 | B2 | 2/2004 | Mackenzie et al. |
| 7,027,875 | B2 | 4/2006 | Siess et al. |
| 8,888,728 | B2 | 11/2014 | Aboul-Hosn et al. |
| 9,937,319 | B1 | 4/2018 | Leeflang et al. |
| 10,709,828 | B2 | 7/2020 | Toellner et al. |
| 10,737,008 | B2 | 8/2020 | Corbett et al. |
| 11,833,314 | B2 | 12/2023 | Corbett et al. |
| 2003/0088213 | A1 | 5/2003 | Schweikert et al. |
| 2004/0210194 | A1* | 10/2004 | Bonnette ................ A61B 17/22 604/167.06 |
| 2005/0197624 | A1 | 9/2005 | Goodson et al. |
| 2006/0047266 | A1 | 3/2006 | Elkins et al. |
| 2008/0033396 | A1 | 2/2008 | Danek et al. |
| 2008/0188831 | A1 | 8/2008 | Bonnette et al. |
| 2009/0259200 | A1 | 10/2009 | Lampropoulos et al. |
| 2010/0036329 | A1 | 2/2010 | Razack |
| 2010/0100044 | A1 | 4/2010 | Ye et al. |
| 2011/0004223 | A1 | 1/2011 | Leeflang et al. |
| 2011/0077621 | A1 | 3/2011 | Graham et al. |
| 2014/0025037 | A1 | 1/2014 | Elkins et al. |
| 2015/0141738 | A1 | 5/2015 | Toellner et al. |
| 2017/0049947 | A1 | 2/2017 | Corbett et al. |
| 2018/0184912 | A1* | 7/2018 | Al-Ali .................. A61M 39/24 |
| 2018/0229008 | A1* | 8/2018 | Blacker .................. A61B 34/00 |
| 2018/0250456 | A1 | 9/2018 | Nitzan et al. |
| 2019/0167967 | A1 | 6/2019 | Mottola et al. |
| 2020/0121905 | A1 | 4/2020 | Zoll |
| 2020/0289794 | A1 | 9/2020 | Fantuzzi |
| 2020/0345337 | A1 | 11/2020 | Muller et al. |
| 2020/0391014 | A1 | 12/2020 | Walters et al. |
| 2021/0085923 | A1 | 3/2021 | Fantuzzi et al. |
| 2023/0270988 | A1 | 8/2023 | Sharma et al. |

FOREIGN PATENT DOCUMENTS

| | | | |
|---|---|---|---|
| JP | 2018522648 | A | 8/2018 |
| WO | 9813083 | A1 | 4/1998 |
| WO | 2016001439 | A1 | 1/2016 |
| WO | 2016210300 | A1 | 12/2016 |
| WO | 2019032520 | A2 | 2/2019 |

* cited by examiner

TUOHY VALVE TIGHTENING PORT FOR PERCUTANEOUS CIRCULATORY SUPPORT DEVICE REPOSITIONING AND AXIAL LOCKING

CROSS-REFERENCE TO RELATED APPLICATION

This application claims priority to U.S. Provisional Application No. 63/316,239, filed Mar. 3, 2022, which is herein incorporated by reference in its entirety.

TECHNICAL FIELD

The present disclosure relates to a locking attachment to a hub of an introducer sheath. More specifically, the present disclosure relates to a Tuohy valve tightening port attachment that allows for repositioning and axial locking of a medical device positioned within a hub of the introducer sheath.

BACKGROUND

In various procedures for delivering intravascular medical devices, an introducer sheath is inserted into a blood vessel of a patient, for example a femoral artery, and medical devices are inserted into the introducer sheath for introduction into the blood vessel. In various instances, the medical devices include catheters or other medical devices such as a blood pump. A hemostasis valve hub may be incorporated at a proximal end of the introducer sheath to reduce blood leakage as devices are being inserted, positioned, and removed. In various instances, there may be a desire for repositioning of the medical device and stabilization of the medical device upon repositioning. There is a need for increased axial stabilization of the medical devices inserted into the valve hub and the introducer sheath while still facilitating passage of the devices through the introducer sheath and allowing for repositioning of the devices.

SUMMARY

In an Example 1, a tightening port for use with a hub of a sheath includes a cartridge for reversible engagement with a proximal end of the hub, the cartridge having a proximal end and a distal end and a lumen extending therebetween, a seal positioned within the lumen of the cartridge, a lock nut having an inner portion positioned within the lumen of the cartridge and an outer portion configured for engagement with the proximal end of the cartridge, such that the inner portion of the lock nut is configured to push the seal to reduce a size of an opening of the seal.

In an Example 2, the tightening port of Example 1 further includes wherein the cartridge has a first portion having a first diameter and a second portion having a second diameter and the first diameter being less than the second diameter.

In an Example 3, the tightening port of Example 2 further includes wherein the first portion of the cartridge comprises at least one post extending radially from the first portion.

In an Example 4, the tightening port of Example 3 further includes wherein the at least one post is configured for engagement with at least one opening of the hub for securing the tightening port to the hub.

In an Example 5, the tightening port of any one of Examples 2-4 further includes wherein an outer surface of the second portion of the cartridge has a plurality of threads extending at least partially around the outer surface.

In an Example 6, the tightening port of Example 5 further includes wherein the outer portion of the lock nut comprises a threaded surface configured for engagement with the plurality of threads of the outer surface of the second portion of the cartridge to secure the lock nut to the cartridge.

In an Example 7, the tightening port of any one of Examples 1-6 further includes wherein the hub is a hemostasis valve hub, the tightening port includes a sleeve holder, and the seal is a Tuohy seal.

In an Example 8, the tightening port of any one of Examples 1-7 further includes a lumen that extends through the cartridge, the seal, and the lock nut such that the lumen is aligned with a longitudinal axis of the tightening port In an Example 9, a delivery system for at least one medical device into a blood vessel includes a sheath having a proximal end and a distal end and configured for insertion through the blood vessel, a hub for engaging with the proximal end of the sheath, and a tightening port for engaging with a proximal end of the hub. The tightening port includes a cartridge for reversible engagement with a proximal end of the hub, the cartridge having a proximal end and a distal end and a lumen extending therebetween, a lumen for receiving the medical device, a seal positioned within the lumen of the cartridge, and a lock nut having an inner portion positioned within the lumen of the cartridge and an outer portion configured for engagement with the proximal end of the cartridge, such that the inner portion of the lock nut is configured to push the seal to engage the seal against the medical device.

In an Example 10, the delivery system of Example 9 further includes wherein the cartridge comprises a first portion having a first diameter, a second portion having a second diameter and wherein the first diameter is less than the second diameter.

In an Example 11, the delivery system of Example 10 further includes wherein the seal is positioned adjacent a transition area between the first portion and the second portion of the cartridge.

In an Example 12, the delivery system of Example 11 further includes wherein the lock nut is configured to axially compress the seal to reduce the size of an opening of the seal.

In an Example 13, a method for delivering at least one medical device into a blood vessel includes inserting a sheath into the blood vessel, the sheath having a proximal end and a distal end and a hub on the proximal end, inserting a catheter through a proximal end of the hub, providing a pre-assembled tightening port having a cartridge over the catheter, the cartridge comprising a seal positioned within the cartridge, a lock nut of the tightening port at least partially within the cartridge and engaging the tightening port with the proximal end of the hub, and engaging the lock nut with the cartridge to axially push the seal such that the seal engages against the catheter and an inner surface of the cartridge.

In an Example 14, the method of Example 13 further includes wherein the cartridge comprises a first portion having a first diameter and a second portion having a second diameter that is greater than the first diameter, and wherein during the engaging of the lock nut, the seal is axially pushed into the first portion, causing reduction in the size of an opening of the seal.

In an Example 15, the method of Example 13 or Example 14 further includes wherein a portion of the cartridge includes an outer surface having a plurality of threads and the lock nut comprises a threaded portion, and wherein engaging the lock nut with the cartridge further includes engaging the threaded portion of the lock nut with the plurality of threads of the cartridge.

In an Example 16, a tightening port for use with a hemostasis valve hub of a sheath includes a cartridge for reversible engagement with a proximal end of the hemostasis valve hub, the cartridge having a proximal end and a distal end and a lumen extending therebetween, a seal positioned within the lumen of the cartridge, a lock nut having an inner portion positioned within the lumen of the cartridge and an outer portion configured for engagement with the proximal end of the cartridge, such that the inner portion of the lock nut is configured to push the seal to reduce a size of an opening of the seal, and a sleeve holder engaged with the lock nut.

In an Example 17, the tightening port of Example 16 further includes wherein the cartridge has a first portion having a first diameter and a second portion having a second diameter and the first diameter being less than the second diameter.

In an Example 18, the tightening port of Example 17 further includes wherein the first portion of the cartridge comprises at least one post extending radially from the first portion.

In an Example 19, the tightening port of Example 18 further includes wherein the at least one post is configured for engagement with at least one opening of the hemostasis valve hub for securing the tightening port to the hemostasis valve hub.

In an Example 20, the tightening port of Example 17 further includes wherein an outer surface of the second portion of the cartridge has a plurality of threads extending at least partially around the outer surface.

In an Example 21, the tightening port of Example 20 further includes wherein the outer portion of the lock nut comprises a threaded surface configured for engagement with the plurality of threads on the outer surface of the second portion of the cartridge to secure the lock nut to the cartridge.

In an Example 22, the tightening port of Example 16 wherein the seal is a Tuohy seal.

In an Example 23, the tightening port of Example 16 further includes a lumen that extends through the cartridge, the seal, and the lock nut such that the lumen is aligned with a longitudinal axis of the tightening port.

In an Example 24, the tightening port of Example 16 further includes wherein the lock nut comprises an extending portion and the sleeve holder defines a lumen, and wherein the extending portion is received within the lumen of the sleeve holder.

In an Example 25, the tightening port of Example 16 further includes wherein the seal is composed of silicone.

In an Example 26, a delivery system for at least one medical device into a blood vessel including a sheath having a proximal end and a distal end and configured for insertion through the blood vessel, a hemostasis valve hub engaging with the proximal end of the sheath, and a tightening port for engaging with a proximal end of the hemostasis valve hub. The tightening port includes a cartridge for reversible engagement with a proximal end of the hub, the cartridge having a proximal end and a distal end and a lumen extending therebetween, a lumen for receiving the medical device, a seal positioned within the lumen of the cartridge, a lock nut having an inner portion positioned within the lumen of the cartridge and an outer portion configured for engagement with the proximal end of the cartridge, such that the inner portion of the lock nut is configured to push the seal to engage the seal against the medical device, and a sleeve holder engaged with the lock nut.

In an Example 27, the delivery system of Example 26 includes wherein the cartridge comprises a first portion having a first diameter, a second portion having a second diameter and wherein the first diameter is less than the second diameter.

In an Example 28, the delivery system of Example 27 further includes wherein the seal is positioned adjacent a transition area between the first portion and the second portion.

In an Example 29, the delivery system of Example 28 further includes wherein the lock nut is configured to axially compress the seal to reduce the size of an opening of the seal.

In an Example 30, a method for delivering at least one medical device in a blood vessel includes inserting a sheath into the blood vessel, the sheath having a proximal end and a distal end and a valve hub on the proximal end of the sheath, inserting a catheter through a proximal end of the valve hub, providing a pre-assembled tightening port having a cartridge over the catheter, the cartridge comprising a seal positioned within the cartridge, a lock nut of a tightening port at least partially within the cartridge and engaging the tightening port with the proximal end of the valve hub, and engaging the lock nut with the cartridge to axially push the seal such that the seal engages against the catheter and an inner surface of the cartridge.

In an Example 31, the method of Example 20 further includes wherein the cartridge comprises a first portion having a first diameter and a second portion having a second diameter that is greater than the first diameter, and wherein during the engaging of the lock nut, the seal is axially pushed into the first portion, causing reduction in the size of an opening of the seal.

In an Example 32, the method of Example 30 further includes wherein a portion of the cartridge includes an outer surface having a plurality of threads and the lock nut comprises a threaded portion, and wherein engaging the lock nut with the cartridge further includes engaging the threaded portion of the lock nut with the plurality of threads of the cartridge.

In an Example 33, the method of Example 30 further includes wherein engaging the cartridge with the proximal end of the valve hub includes engaging at least one post of the cartridge with at least one opening of the valve hub.

In an Example 34, the method of Example 30 further includes inserting a blood pump into the catheter.

In an Example 35, the method of Example 30 further includes loosening the engagement between the lock nut and the cartridge and repositioning the catheter.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
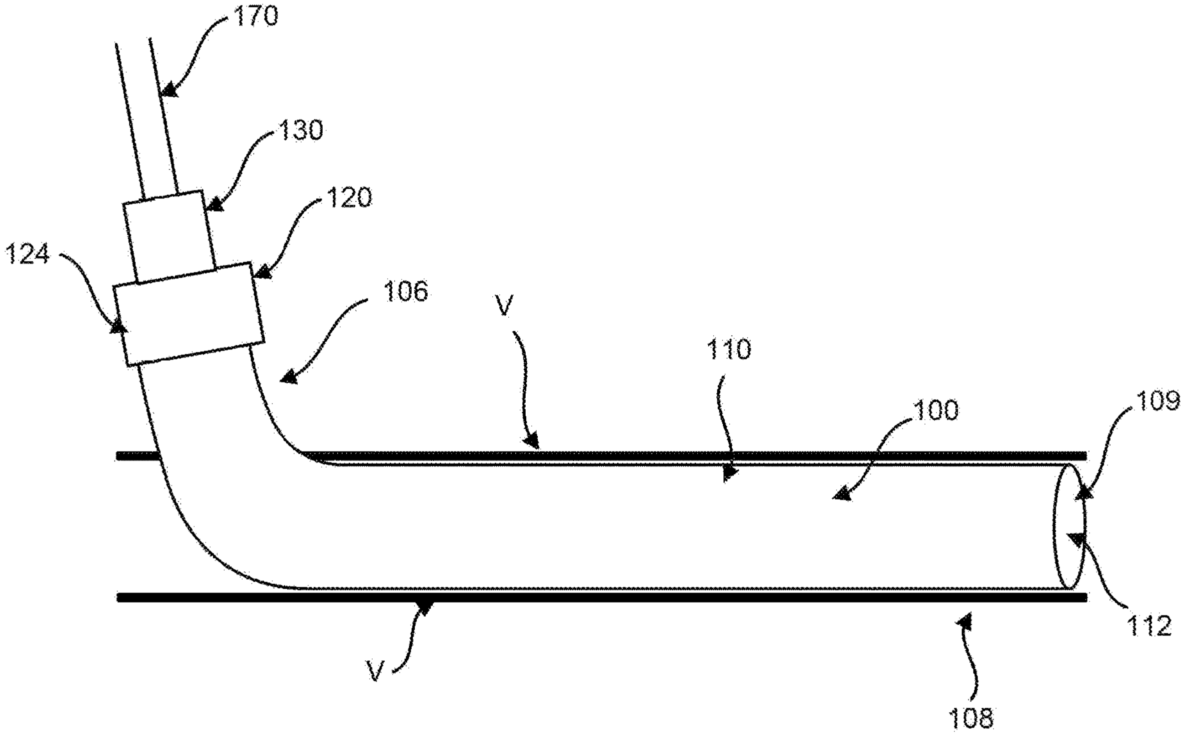
FIG. 1 illustrates a cross sectional view of an introducer sheath extending to an introducer sheath, in accordance with embodiments of the present disclosure.
Figure 2:
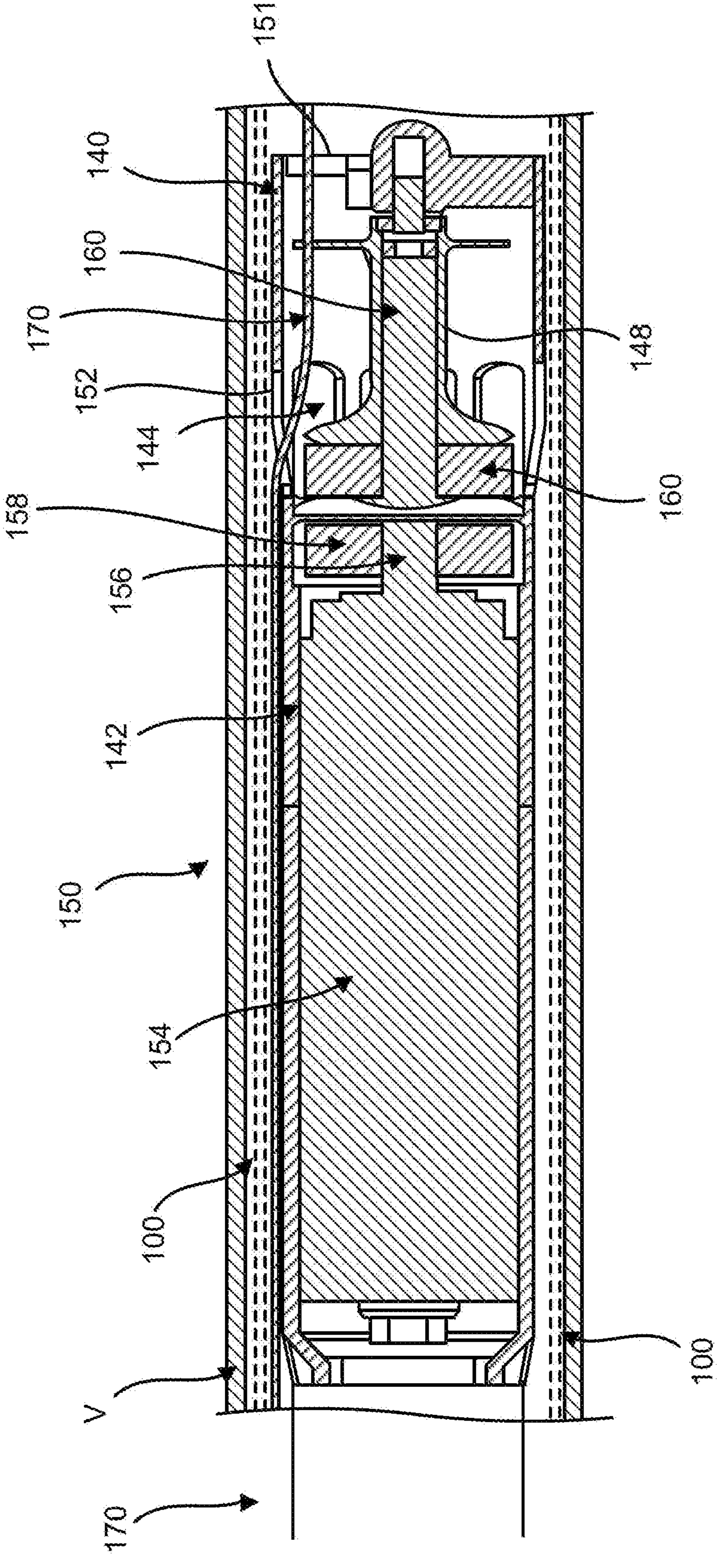
FIG. 2 illustrates a cross sectional view of a medical device positioned within a blood vessel, in accordance with embodiments of the present disclosure.

FIG. 1 illustrates a cross sectional view of a blood vessel V with a sheath 100, such as an introducer sheath 100, inserted at least partially into the blood vessel V. In some embodiments, the introducer sheath 100 is used for facilitating the passage of various relatively large medical devices, such as a blood pump as will be described further herein, through the introducer sheath 100 and into the blood vessel V. Hence, introducer sheath 100 may be referred to as a large bore introducer sheath. The introducer sheath 100 comprises a proximal end 106 and a distal end 108 that is opposite the proximal end 106. The introducer sheath 100 includes a proximal opening (not shown) adjacent the proximal end 106 and a distal opening 109 adjacent the distal end 108. A body portion 110 of the introducer sheath 100 extends between the proximal end 106 and the distal end 108, and the body portion 110 defines a lumen 112 of the introducer sheath 100. The introducer sheath 100 may be formed by various polymeric or metallic materials. In further embodiments, the introducer sheath 100 may comprise an additional surface coating. The surface coating may include, but is not limited to, silicone, PET, or any other applicable polymer. A hub 120 is commonly included at the proximal opening 107. The hub 120, also referred to herein as a hemostasis valve hub, is configured for hemostasis, i.e, to prevent blood from leaking out of the introducer sheath 100 during use. While described herein as a hemostasis valve hub, a different embodiment of a hub may be incorporated. A medical device, for example a catheter 170, may be inserted through the hub 120 and the introducer sheath 100 and the hub 120 may maintain hemostasis between the catheter 170, the introducer sheath 100 and the external surroundings. In some embodiments, the catheter 170 may couple to a distally extending medical device, as the blood pump 150 as shown in FIG. 2. After insertion of the catheter 170, axial stabilization of the catheter 170 may be desired to ensure that it (and any coupled medical device) does not shift axial positioning during use. Further, in these instances, it may also be desired for the operator to reposition the catheter 170 (and any coupled medical device) after insertion in order to place it in the desired positioning throughout operation. As such, a tightening port 130 may be positioned on a proximal end of the hub 120 to provide for axial securement or stabilization of the catheter 170. The tightening port 130 may also facilitate the repositioning and stabilization of the catheter 170, as will be described further herein.

In some embodiments, the sheath 100 may be a repositioning sheath.

FIG. 2 illustrates a cross-sectional view of the introducer sheath 100 of FIG. 1 after insertion of a medical device, illustratively a blood pump 150, into the introducer sheath 100. As noted above, in some embodiments a catheter, such as the catheter 170, may be coupled to the proximal end of the blood pump 150 and extend outside the blood vessel V. The blood pump 150 generally includes an impeller assembly housing 140 and a motor housing 142. In some embodiments, the impeller assembly housing 140 and the motor housing 142 may be integrally or monolithically constructed. The impeller assembly housing 140 carries an impeller assembly 144 therein. The impeller assembly 144 includes an impeller shaft 146 and an impeller 148 that rotates relative to the impeller assembly housing 140 to drive blood through the blood pump 150. More specifically, the impeller 148 causes blood to flow from a blood inlet 151 formed on the impeller assembly housing 140, through the impeller assembly housing 140, and out of a blood outlet 152 formed on the impeller assembly housing 140. In some embodiments the impeller shaft 146 and the impeller 148 may be integrated, and in other embodiments the impeller shaft 146 and the impeller 148 may be separate components. As shown in FIG. 2, the inlet 151 may be formed on an end portion of the impeller assembly housing 140 and the outlet 152 may be formed on a side portion of the impeller assembly housing 140. In other embodiments, the inlet 151 and/or the outlet 152 may be formed on other portions of the impeller assembly housing 140. In some embodiments, the impeller assembly housing 140 may couple to a distally extending cannula (not shown), and the cannula may receive and deliver blood to the inlet 151.

With continued reference to FIG. 2, the motor housing 142 carries a motor 154, and the motor 154 is configured to rotatably drive the impeller 148 relative to the impeller assembly housing 140. In the illustrated embodiment, the motor 154 rotates a drive shaft 156, which is coupled to a driving magnet 158. Rotation of the driving magnet 158 causes rotation of a driven magnet 160, which is connected to the impeller assembly housing 140. More specifically, in embodiments incorporating the impeller shaft 146, the impeller shaft 146 and the impeller 148 are configured to rotate with the driven magnet 160. In other embodiments, the motor 154 may couple to the impeller assembly housing 140 via other components. As noted above, in some embodiments and as illustrated in FIG. 2, the catheter 170 extends from a proximal end of the blood pump 150 and may be coupled to the motor housing 142 through a tapering connector and/or various other connecting means. While the introducer sheath 100 is illustrated above with the use of the blood pump 150, various other medical devices may be used in conjunction with the introducer sheath 100 and the hemostasis valve hub 120. For example, another variation of a blood pump may be used in conjunction with the introducer sheath 100. In other examples, a medical device other than a blood pump may be incorporated.

Figure 3:
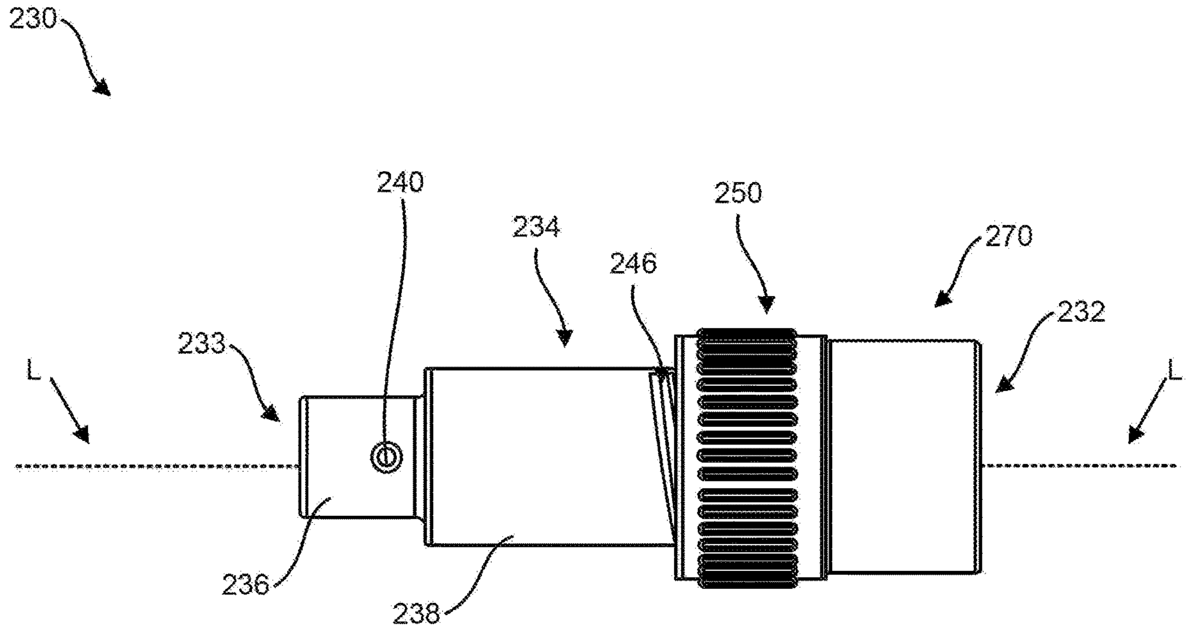
FIG. 3 illustrates a side view of a tightening port for use with a valve hub, in accordance with embodiments of the present disclosure.
Figure 4:
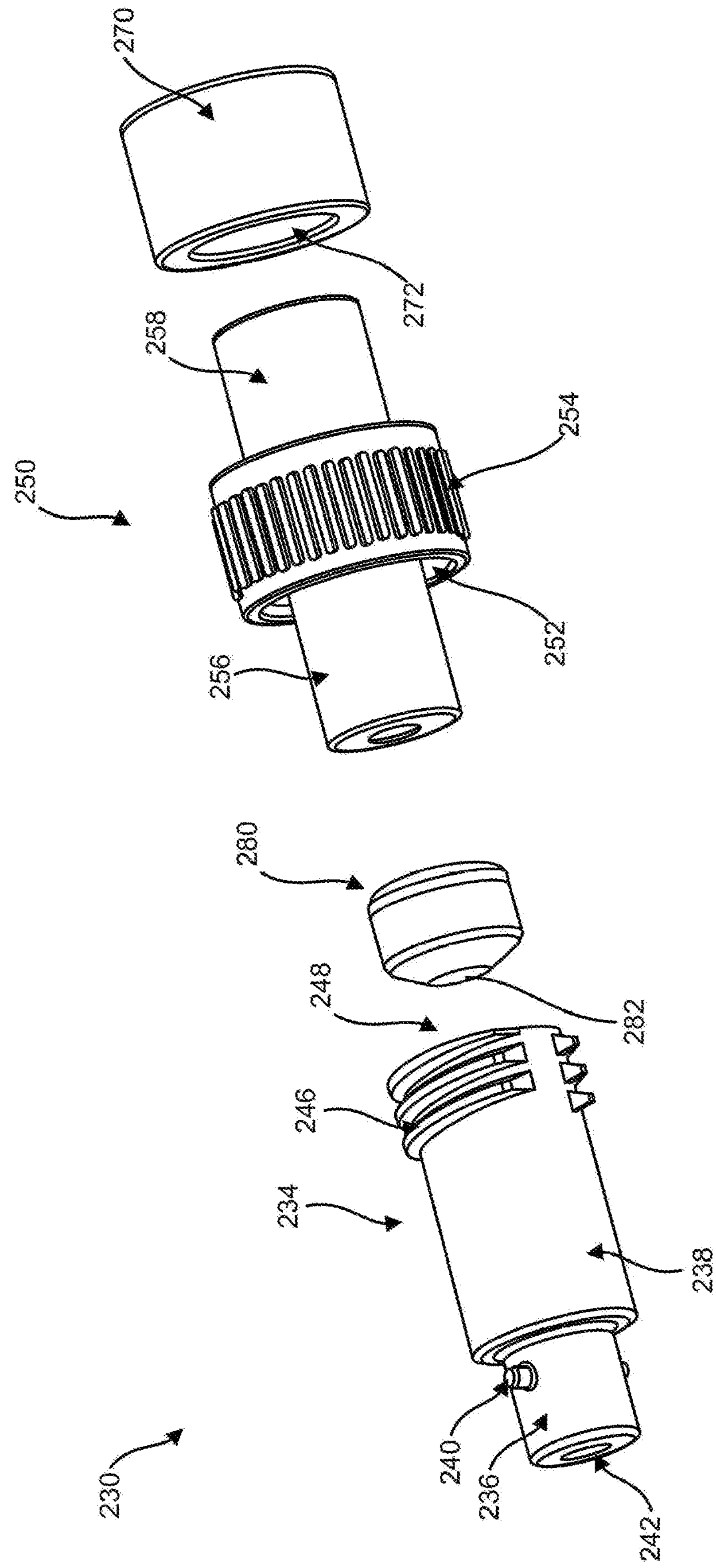
FIG. 4 illustrates an exploded view of the tightening port as shown in FIG. 3, in accordance with embodiments of the present disclosure.

FIGS. 3 and 4 illustrate an embodiment of a tightening port 230 configured for attachment to the hub 120. The tightening port 230 includes a proximal end 232 and a distal end 233 and extends along a longitudinal axis L. Adjacent the distal end 233, the tightening port 230 comprises a cartridge 234 configured for engaging a lock nut 250 which may engage a sleeve holder 270. As illustrated, at the distal end 233, the cartridge 234 comprises an opening 242. The opening 242 may define a portion of a lumen 244 (FIG. 7) for receiving a medical device, for example the catheter 170

(FIG. 1), as will be described further herein. Additionally, the cartridge 234 comprises a first portion 236 defined by a first diameter D1 (FIG. 7) and a second portion 238 defined by a second diameter D2 (FIG. 7). The first portion 236 comprises at least one post 240 extending radially outward from an outer surface of the first portion 236 for engaging with the hub 120. In some embodiments, the at least one post 240 includes two posts. In other embodiments, the at least one post 240 may include three or more posts. The second portion 238 of the cartridge 234 comprises a plurality of threads 246 that extend radially outward from an outer surface of the second portion 238. As illustrated, the threads 246 may be configured for engaging with a mating threaded portion 252 of the lock nut 250. More specifically, the lock nut 250 comprises an outer portion 254 having an inner surface that defines the threaded portion 252 which is configured for engagement with an outer surface of the second portion 238, as will be described further with reference to FIGS. 6 and 7. The lock nut 250 additionally comprises an inner portion 256 configured for extending at least within the second portion 238 of the cartridge 234 after engagement, as will be described further herein with reference to FIG. 7.

Further, the tightening port 230 comprises a seal 280 that is received within the cartridge 234. More specifically, upon assembly the seal 280 is positioned within the second portion 238 and positioned adjacent the first portion 236. The seal 280 is generally cylindrical in shape with an opening 282 extending through a center of the seal 280 and defining a lumen which may align with the opening 242 of the cartridge 234 to extend the lumen 244. In various embodiments, the seal 280 is a Tuohy seal. In some embodiments, the seal 280 is composed of silicone, or various other suitable materials like polymer, thermoset, rubber, or thermoset elastomer (TSE), silicone rubber. The seal 280 will be described further herein with reference to FIG. 7.

With reference still to FIGS. 3-4, the lock nut 250 comprises an extension portion 258 that extends proximally from the outer portion 254. The extension portion 258 is configured for receiving the sleeve holder 270. The sleeve holder 270 comprises a generally cylindrical orientation to define a lumen 272. The lumen 272 of the sleeve holder 270 receives the extension portion 258 of the lock nut 250 and may be configured for securing the positioning of a sterile sleeve positioned over the lock nut 250 and within the lumen 272 of the sleeve holder 270.

Figure 5:
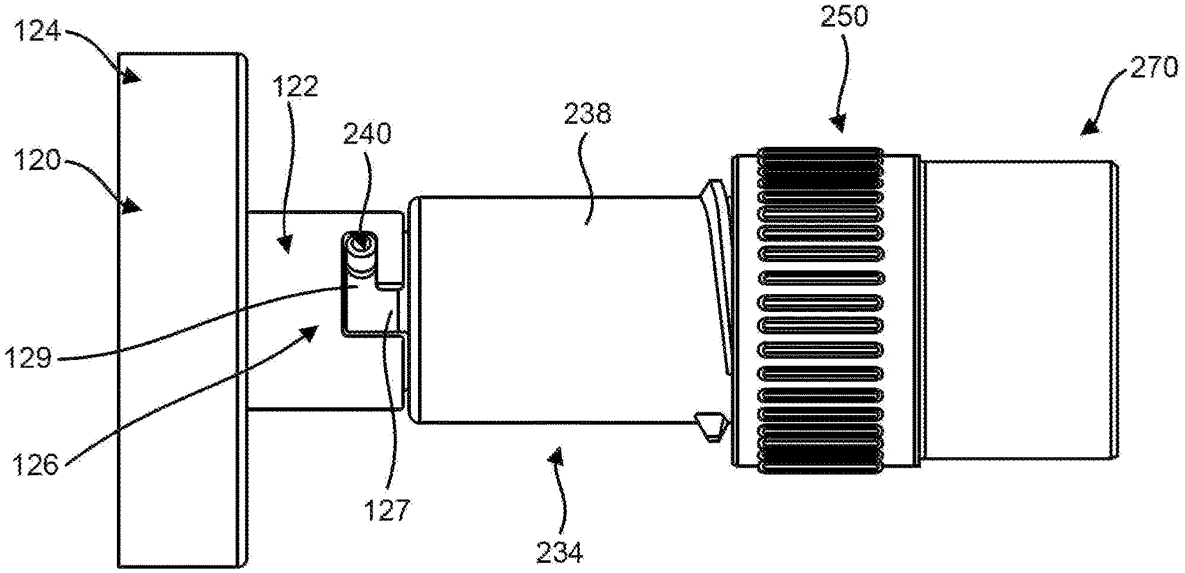
FIG. 5 illustrates a side view of a portion of a tightening port, in accordance with embodiments of the present disclosure.

As disclosed above, the cartridge 234 may be configured for engaging with the hub 120 (FIG. 1) to secure the tightening port 230 onto the hub 120. FIG. 5 illustrates the cartridge 234 engaged with the hub 120. More specifically, as illustrated, the hub 120 comprises an extending portion 122 extending from a proximal end 124 of the hub 120. The extending portion 122 comprises a plurality of openings 126 configured for receiving the cartridge 234. The openings 126 comprise a first portion 127 extending aligned with the longitudinal axis L (FIG. 1) of the tightening port 230 and a second portion 129 approximately aligned perpendicularly with the longitudinal axis L. As such, upon insertion of the cartridge 234 into the extending portion 122 of the hub 120, the at least one post 240 is received within the first portion 127 of the hub 120 and the cartridge 234 may be rotated such that the at least one post 240 is received within the second portion 129 of the openings 126 to secure the cartridge 234 with the hub 120. This couples the cartridge 234 within the hub 120 (FIG. 1) and over the medical device inserted through the introducer sheath 100 (FIG. 1). After insertion of the cartridge 234, the lock nut 250 may be engaged with the cartridge 234, as will be described further with reference to FIG. 6.

Figure 6:
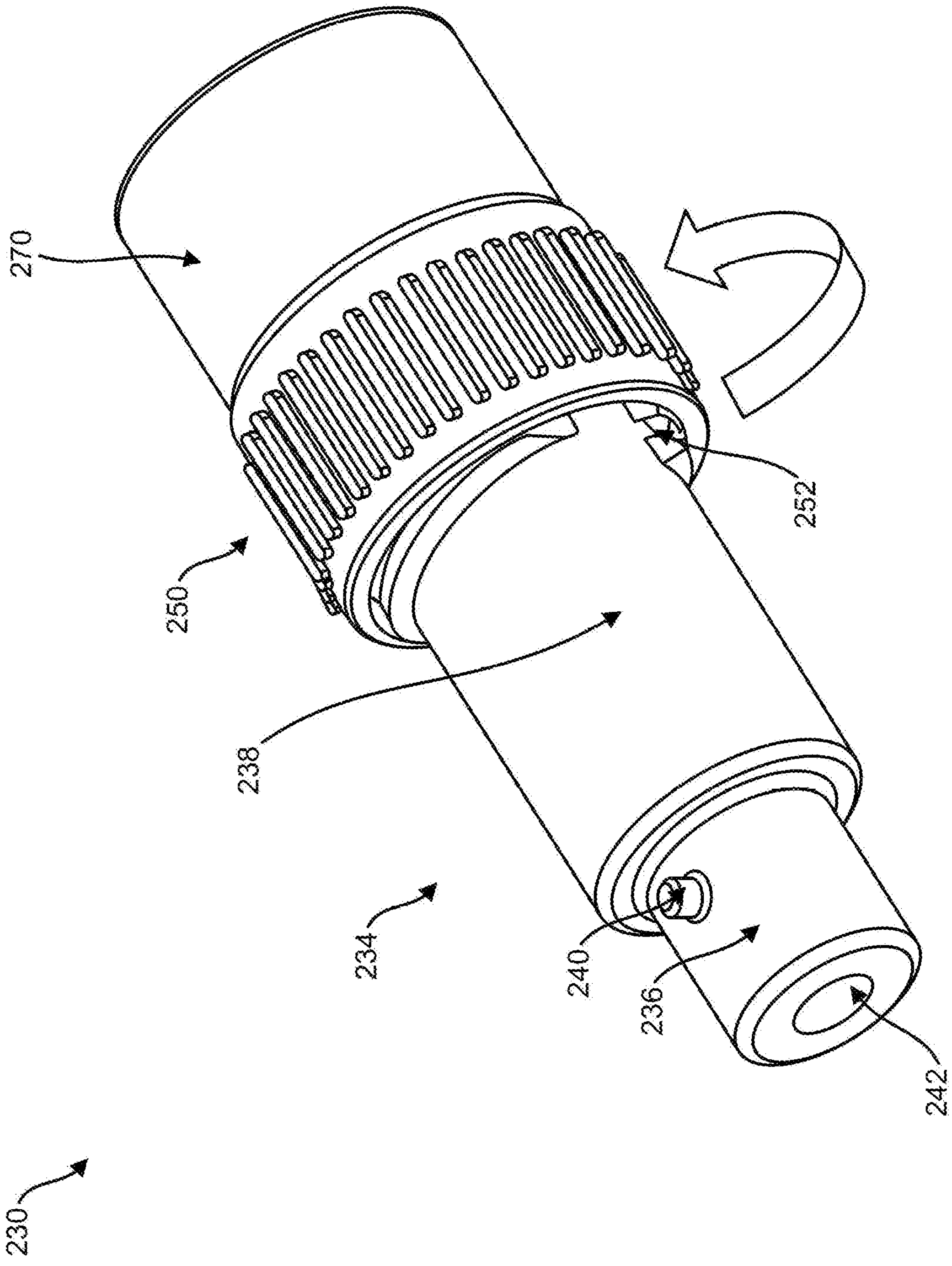
FIG. 6 illustrates a perspective view of the tightening port of FIG. 3, in accordance with embodiments of the present disclosure.
Figure 7:
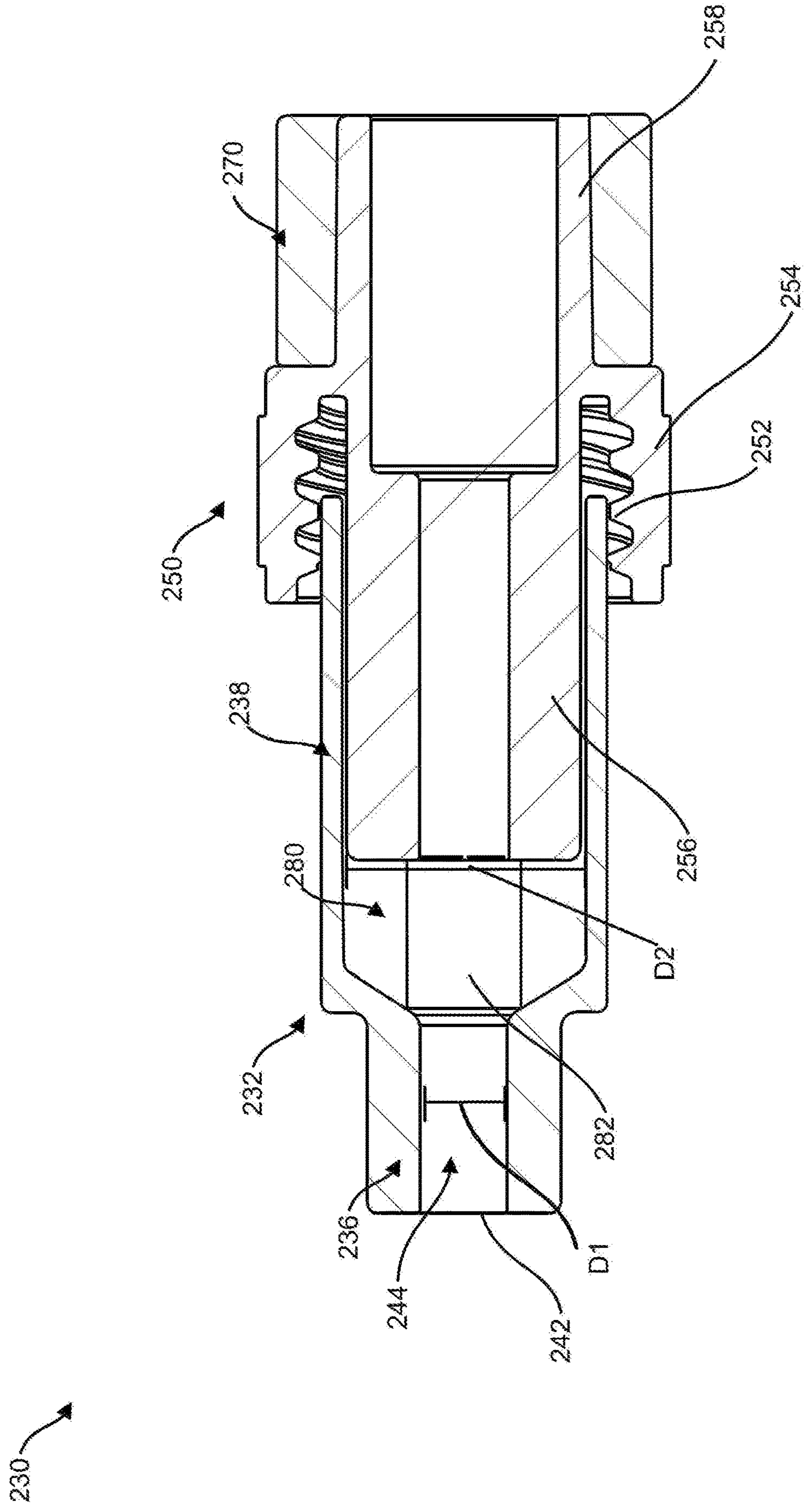
FIG. 7 illustrates a cross sectional view of the tightening port shown in FIG. 3, in accordance with embodiments of the present disclosure.

FIG. 6 illustrates an embodiment of the cartridge 234 during engagement with the lock nut 250. More specifically, in order to engage the cartridge 234 with the lock nut 250, the lock nut 250 is positioned at a proximal end 248 of the cartridge 234, and the threaded portion 252 of the lock nut 250 is engaged with the cartridge 234. In other words, the threaded portion 252 is threadedly engaged with the threads 246 and the lock nut 250 is rotated by the operator in order to tighten the lock nut 250 onto the cartridge 234. As the lock nut 250 is tightened onto the cartridge 234, the seal 280 may be axially pushed by the inner portion 256 of the lock nut 250, as will be described further herein with reference to FIG. 7.

FIG. 7 illustrates the tightening port 230 after engagement of the cartridge 234, the lock nut 250 and the sleeve holder 270. The seal 280 is positioned within the lumen 244 of the tightening port 230, and more specifically, positioned within the cartridge 234. As illustrated, the seal 280 is positioned at a transition point of the cartridge 234, wherein the first portion 236 transitions into the second portion 238 and the diameter increases from the first diameter D1 to the second diameter D2. As previously mentioned, during engagement of the lock nut 250 and the cartridge 234, the inner portion 256 is positioned within the cartridge 234 while the threaded portion 252 is positioned around the outer surface of the cartridge 234. As illustrated in FIG. 7, once the lock nut 250 is tightened into engagement with the cartridge 234, the inner portion 256 may be in direct contact with the seal 280. During engagement and displacement of the inner portion 256 further distally into the cartridge 234, the inner portion 256 axially pushes the seal 280. Due to the positioning of the seal 280 near the transition point between the first portion 236 and the second portion 238 of the cartridge 234, the axial pushing of the seal 280 causes the seal 280 to move adjacent the first portion 236 of smaller diameter D1. Once the seal 280 is positioned adjacent the first portion 236, further axial pushing of the seal 280 causes axial compression of the seal 280. In turn, the size of the opening 282 of the seal 280 is reduced during and after the axial compression of the seal 280. Reduction in size of the opening 282 of the seal 280 causes engagement between the seal 280 and the medical device extending through the tightening port 230, for example the catheter 170 (FIG. 1), and axial compression of the seal 280 causes engagement of the seal 280 with the inner surface of the cartridge 234. In other words, the axial compression of the seal 280 causes the opening 228, and thus the lumen, to decrease while the seal 280 also expands outwardly to contact the inner surface of the cartridge 234. More specifically, the decrease in the size of the opening 282 and thus the lumen of the seal 280 causes the seal 280 to tighten around the catheter 170 while also causing the seal 280 to expand, for example radially and/or axially, against an inner surface of the cartridge 234 for engagement with the cartridge 234. In this way, the catheter 170 is secured and stabilized, such that radial or axial movement of the catheter 170 (and any coupled medical device) is substantially reduced or eliminated. The lock nut 250 may then be loosened through rotation of the lock nut 250 by the operator, resulting in decreased engagement between the catheter 170 and seal 280, so that the axial position of catheter 170 can be adjusted. Once the catheter 170 (and any coupled medical device) is in the desired position, the lock nut 250 can be tightened again and the axial position of the catheter 170 secured. In this way, the tightening port 230 provides a method of axially stabilizing a medical device, for example the catheter 170 (and any coupled medical device), without requiring the removal of the introducer sheath 100, the hub 120 and/or the tightening port 230.

Figure 8:
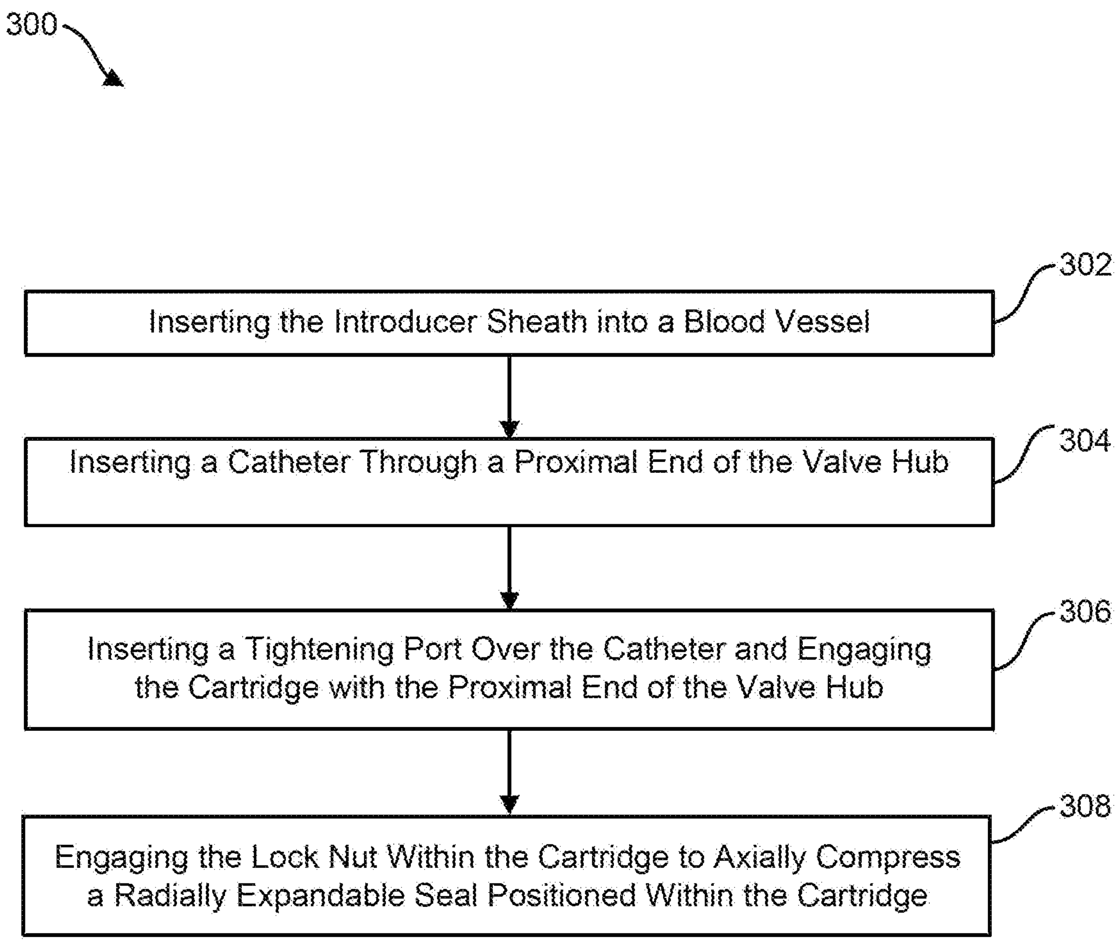
FIG. 8 illustrates a flow chart for a method of delivering at least one medical device into a blood vessel, in accordance with embodiments of the present disclosure.

Further, with reference to the above-described figures and FIG. 8, a method 300 of delivering a medical device into the blood vessel V is described. For example, the medical device may include the catheter 170 which may then be configured for receiving the blood pump 150 (FIG. 1) for delivery into the blood vessel V. However, while described with reference to delivery of catheter 170, various other devices may be used.

At block 302, the method 300 then includes inserting the introducer sheath 100 into the blood vessel V. At block 304, the method 300 includes inserting a medical device, for example the catheter 170, into and through the proximal end 124 of the hub 120 so that the catheter 170 extends through the hub 120 and into the introducer sheath 100.

At block 306, the method 300 may include inserting the tightening port 230 over the catheter 170 and engaging the cartridge 234 with the extending portion 122 of the hub 120. However, in other embodiments, the tightening port 230 may be preassembled on the introducer sheath 100 or on a medical device, such as catheter 170, before insertion of the medical device through the hub 120. In such embodiments, the tightening port 230 may be already be positioned on the introducer sheath or hub 120 when catheter 170 is inserted through the introducer sheath 100 and the hub 120. At block 308, the method 300 further includes tightening the lock nut 250 with the cartridge 234 to push the seal 280 and axially compress the seal to reduce the radial size of the opening 282 of the seal 280. In some embodiments, this step includes engaging the threaded portion 252 of the lock nut 250 with the plurality of threads 246 of the cartridge 234 such that the inner portion 256 axially compresses against the seal 280. As previously described, this in turn causes expansion of the seal 280 into engagement with the exterior surface of the catheter 170 and the inner surface of the cartridge 234. As such, the catheter 170 is axially secured within the tightening port 230 after engagement of the lock nut 250 and the cartridge 234. The method 300 may also include loosening the engagement between the lock nut 250 and the cartridge 234. In other words, the lock nut 250 may be rotated to release engagement between the threaded portion 252 and the threads 246 of the cartridge 234. In this way, the operator can reposition the catheter 170 before repeating the engagement between the lock nut 250 and the cartridge 234 to once again secure the axial positioning of the catheter 170. In various embodiments, the method further includes inserting the blood pump 150 coupled to the catheter 170 through the introducer sheath 100 for delivery into the blood vessel V.

While the embodiments and method are described with reference to the catheter 170 and the blood pump 150 for reception into the catheter 170, various other medical devices may be incorporated. Various modifications and additions can be made to the exemplary embodiments discussed without departing from the scope of the present invention. For example, while the embodiments described above refer to particular features, the scope of this invention also includes embodiments having different combinations of features and embodiments that do not include all of the above-described features.

The invention claimed is:

1. A tightening port for use with a hemostasis valve hub of a sheath, the port comprising:

a cartridge for reversible engagement with a proximal end of the hemostasis valve hub, the cartridge having a proximal end and a distal end and a lumen extending therebetween;

a seal positioned within the lumen of the cartridge;

a lock nut having an inner portion positioned within the lumen of the cartridge and an outer portion configured for engagement with the proximal end of the cartridge, such that the inner portion of the lock nut is configured to extend distally from the outer portion into the lumen of the cartridge, to push the seal to reduce a size of an opening of the seal; and a sleeve holder circumferentially surrounding and engaged with a proximal end of the lock nut.

2. The tightening port of claim 1, wherein the cartridge has a first portion having a first diameter and a second portion having a second diameter and the first diameter being less than the second diameter.

3. The tightening port of claim 2, wherein the first portion of the cartridge comprises at least one post extending radially from the first portion.

4. The tightening port of claim 3, wherein the at least one post is configured for engagement with at least one opening of the hemostasis valve hub for securing the tightening port to the hemostasis valve hub.

5. The tightening port of claim 2, wherein an outer surface of the second portion of the cartridge has a plurality of threads extending at least partially around the outer surface.

6. The tightening port of claim 5, wherein the outer portion of the lock nut comprises a threaded surface configured for engagement with the plurality of threads on the outer surface of the second portion of the cartridge to secure the lock nut to the cartridge.

7. The tightening port of claim 1, wherein the seal is a Tuohy seal.

8. The tightening port of claim 1, wherein the tightening port comprises a lumen that extends through the cartridge, the seal, and the lock nut such that the lumen is aligned with a longitudinal axis of the tightening port.

9. The tightening port of claim 1, wherein the lock nut comprises a proximally extending portion and the sleeve holder defines a lumen, and wherein the proximally extending portion is received within the lumen of the sleeve holder.

10. The tightening port of claim 1, wherein the seal is composed of silicone.

11. A delivery system for at least one medical device into a blood vessel, the delivery system comprising:

a sheath having a proximal end and a distal end and configured for insertion through the blood vessel;

a hemostasis valve hub engaging with the proximal end of the sheath; and a tightening port for engaging with a proximal end of the hemostasis valve hub, the tightening port comprising:

a cartridge for reversible engagement with a proximal end of the hemostasis valve hub, the cartridge having a proximal end and a distal end and a lumen extending therebetween;

a lumen for receiving the at least one medical device;

a seal positioned within the lumen of the cartridge;

a lock nut having an inner portion positioned within the lumen of the cartridge and an outer portion configured for engagement with the proximal end of the cartridge, such that the inner portion of the lock nut is configured to extend distally from the outer portion into the lumen of the cartridge, to push the seal to reduce a size of an opening of the seal; and a sleeve holder circumferentially surrounding and engaged with a proximal end of the lock nut.

12. The delivery system of claim 11, wherein the cartridge comprises a first portion having a first diameter, a second portion having a second diameter and wherein the first diameter is less than the second diameter.

13. The delivery system of claim 12, wherein the seal is positioned adjacent a transition area between the first portion and the second portion.

14. The delivery system of claim 13, wherein the lock nut is configured to axially compress the seal to reduce the size of an opening of the seal.

* * * * *